(12) United States Patent
Rivers et al.

(10) Patent No.: US 8,758,377 B2
(45) Date of Patent: *Jun. 24, 2014

(54) ECCENTRIC ABRADING AND CUTTING HEAD FOR HIGH-SPEED ROTATIONAL ATHERECTOMY DEVICES

(75) Inventors: Jody Rivers, Elk River, MN (US); Chuck Plowe, Hugo, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 500 days.

This patent is subject to a terminal disclaimer.

(21) Appl. No.: 12/130,024

(22) Filed: May 30, 2008

(65) Prior Publication Data

US 2009/0299391 A1    Dec. 3, 2009

(51) Int. Cl.
*A61B 17/22* (2006.01)

(52) U.S. Cl.
USPC .......................................................... 606/159

(58) Field of Classification Search
USPC ......... 606/159, 167, 170, 171, 180, 194, 200; 604/22
See application file for complete search history.

(56) References Cited

U.S. PATENT DOCUMENTS

| | | | |
|---|---|---|---|
| 4,445,509 A | 5/1984 | Auth |
| 4,646,736 A | 3/1987 | Auth |
| 4,728,319 A | 3/1988 | Masch |
| 4,883,460 A | 11/1989 | Zanetti |
| 4,935,025 A | 6/1990 | Bundy et al. |
| 4,990,134 A | 2/1991 | Auth |
| 5,007,896 A | 4/1991 | Shiber |
| 5,026,384 A | 6/1991 | Farr et al. |
| 5,030,201 A | 7/1991 | Palestrant |
| 5,041,082 A | 8/1991 | Shiber |
| 5,078,723 A | 1/1992 | Dance et al. |
| 5,116,352 A | 5/1992 | Schnepp-Pesch et al. |
| 5,158,564 A | 10/1992 | Schnepp-Pesch et al. |
| 5,192,291 A | 3/1993 | Pannek, Jr. |
| 5,217,474 A | 6/1993 | Zacca et al. |
| 5,224,945 A | 7/1993 | Pannek, Jr. |
| 5,226,909 A | 7/1993 | Evans et al. |
| 5,267,955 A | 12/1993 | Hanson |

(Continued)

FOREIGN PATENT DOCUMENTS

| | | |
|---|---|---|
| GB | 2 426 456 | 11/2006 |
| WO | 99/08609 | 2/1999 |
| WO | WO2008/073749 | 6/2008 |

OTHER PUBLICATIONS

International Search Report for PCT/US2010/045417, dated Oct. 6, 2010.

*Primary Examiner* — Katherine M Shi

(74) *Attorney, Agent, or Firm* — Winthrop & Weinstine, P.A.

(57) ABSTRACT

The invention provides a rotational atherectomy device having, in various embodiments, a flexible, elongated, rotatable drive shaft with at least one flexible or inflexible eccentric enlarged abrading and cutting head attached thereto which comprises an abrasive surface. When placed against stenotic tissue and rotated at high speed, the eccentric nature of the abrading and cutting head moves along an orbital path, opening the lesion to a diameter larger than the resting diameter of the enlarged abrading and cutting head. Preferably the abrading and cutting head has a center of mass spaced radially from the rotational axis of the drive shaft, facilitating the ability of the device to travel along an orbital path. The abrading and cutting head comprises proximal and/or distal radiused surfaces that facilitate cutting difficult stenosis material while minimizing trauma to the vessel.

38 Claims, 12 Drawing Sheets

(56) References Cited

U.S. PATENT DOCUMENTS

| | | |
|---|---|---|
| 5,308,354 A | 5/1994 | Zacca et al. |
| 5,312,427 A | 5/1994 | Shturman |
| 5,314,438 A | 5/1994 | Shturman |
| 5,372,602 A | 12/1994 | Burke |
| 5,376,100 A | 12/1994 | Lefebvre |
| 5,395,311 A | 3/1995 | Andrews |
| 5,431,673 A | 7/1995 | Summers et al. |
| 5,443,443 A | 8/1995 | Shiber |
| 5,490,859 A | 2/1996 | Mische et al. |
| 5,501,694 A | 3/1996 | Ressemann et al. |
| 5,540,707 A | 7/1996 | Ressemann et al. |
| 5,556,408 A | 9/1996 | Farhat |
| 5,584,843 A | 12/1996 | Wulfman et al. |
| 5,632,755 A | 5/1997 | Nordgren et al. |
| 5,643,298 A | 7/1997 | Nordgren et al. |
| 5,667,490 A | 9/1997 | Keith et al. |
| 5,681,336 A | 10/1997 | Clement et al. |
| 5,836,868 A | 11/1998 | Ressemann et al. |
| 5,843,103 A | 12/1998 | Wulfman |
| 5,916,227 A | 6/1999 | Keith et al. |
| 5,938,670 A | 8/1999 | Keith et al. |
| 6,015,420 A | 1/2000 | Wulfman et al. |
| 6,080,171 A | 6/2000 | Keith et al. |
| RE36,764 E | 7/2000 | Zacca et al. |
| 6,132,444 A | 10/2000 | Shturman et al. |
| 6,146,395 A | 11/2000 | Kanz et al. |
| 6,152,938 A | 11/2000 | Curry |
| 6,206,898 B1 | 3/2001 | Honeycutt et al. |
| 6,270,509 B1 | 8/2001 | Barry et al. |
| 6,494,890 B1 | 12/2002 | Shturman et al. |
| 6,596,005 B1 | 7/2003 | Kanz et al. |
| 2003/0125756 A1* | 7/2003 | Shturman et al. ............ 606/159 |
| 2003/0199889 A1 | 10/2003 | Kanz et al. |
| 2003/0216668 A1 | 11/2003 | Howland et al. |
| 2005/0149083 A1 | 7/2005 | Prudnikov et al. |
| 2005/0149084 A1* | 7/2005 | Kanz et al. .................... 606/159 |
| 2007/0016232 A1 | 1/2007 | St. Martin et al. |
| 2008/0300610 A1 | 12/2008 | Chambers |
| 2008/0306498 A1 | 12/2008 | Thatcher et al. |
| 2009/0131913 A1 | 5/2009 | Grandfield et al. |

* cited by examiner

ECCENTRIC ABRADING AND CUTTING HEAD FOR HIGH-SPEED ROTATIONAL ATHERECTOMY DEVICES

BACKGROUND OF THE INVENTION

1. Field of the Invention

The invention relates to devices and methods for removing tissue from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses an known atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

U.S. Pat. No. 5,681,336 (Clement) provides a known eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

Commonly assigned U.S. patent application Ser. No. 11/761,128 entitled Eccentric Abrading Head for High-Speed Rotational Atherectomy Devices, discloses certain embodiments of an eccentric abrading head. Specifically, Ser. No. 11/761,128 a flexible, elongated, rotatable drive shaft with at least one flexible, or non-flexible, eccentric enlarged abrading head attached thereto, wherein at least part of the eccentric enlarged cutting head has a tissue removing surface—typically an abrasive surface. In certain embodiments, the abrading head will be at least partially hollow. When placed within an artery against stenotic tissue and rotated at sufficiently high speeds the eccentric nature of the enlarged cutting head causes the cutting head and drive shaft to rotate in such a fashion as to open the stenotic lesion to a diameter substantially larger than the outer diameter of the enlarged cutting head. Preferably the eccentric enlarged cutting head has a center of mass spaced radially from the rotational axis of the drive shaft, facilitating the ability of the device to open the stenotic lesion to a diameter substantially larger than the outer diameter of the enlarged cutting head when operated at high speeds.

The eccentric abrading head disclosed in application Ser. No. 11/761,128 comprises proximal, distal and intermediate surfaces. The proximal and distal surfaces are disclosed as each having a leading edge surface that is substantially perpendicular to the drive shaft to which the device is attached. This raised edge surface may make it more difficult to navigate difficult stenoses without damaging the vessel lining and could be improved upon. The disclosure of application Ser. No. 11/761,128 is incorporated herein in its entirety insofar as it discloses the features discussed supra.

The present invention overcomes these deficiencies and provides, inter alia, the above-referenced improvements.

BRIEF SUMMARY OF THE INVENTION

The invention provides a rotational atherectomy device having, in various embodiments, a flexible, elongated, rotatable drive shaft with at least one flexible or inflexible eccentric enlarged abrading and cutting head attached thereto which comprises an abrasive surface. When placed against stenotic tissue and rotated at high speed, the eccentric nature of the abrading and cutting head moves along an orbital path, opening the lesion to a diameter larger than the resting diameter of the enlarged abrading and cutting head. Preferably the abrading and cutting head has a center of mass spaced radially from the rotational axis of the drive shaft, facilitating the ability of the device to travel along an orbital path. The abrading and cutting head comprises proximal and/or distal radiused surfaces that facilitate cutting difficult stenosis material while minimizing trauma to the vessel.

An object of the invention is to provide a high-speed rotational atherectomy device having at least one at least partially flexible eccentric abrading and cutting head having at least one abrasive surface for abrading and proximal and/or distal radiused edges to facilitate entry into stenoses with minimal vessel trauma.

Another object of the invention is to provide a high-speed rotational atherectomy device having at least one non-flexible eccentric abrading and cutting head having at least one abrasive surface for abrading and proximal and/or distal radiused edges to facilitate entry into stenoses with minimal vessel trauma.

Another object of the invention is to provide a high-speed rotational atherectomy device having at least one at least partially flexible eccentric abrading and cutting head radiused edges to facilitate entry into stenoses with minimal vessel trauma and having a resting diameter smaller than its high-speed rotational diameter.

Another object of the invention to provide a high-speed rotational atherectomy device having at least one non-flexible eccentric abrading and cutting head radiused edges to facilitate entry into stenoses with minimal vessel trauma and having a resting diameter smaller than its high-speed rotational diameter.

Another object of the invention is to provide a high-speed rotational atherectomy device having at least one partially flexible eccentric abrading and cutting head with proximal and/or distal radiused edges and that is capable of opening pilot holes in stenoses that nearly or completely block the subject blood vessel with minimal vessel trauma.

Another object of the invention is to provide a high-speed rotational atherectomy device having at least one non-flexible eccentric abrading and cutting head with proximal and/or distal radiused edges and that is capable of opening pilot holes in stenoses that nearly or completely block the subject blood vessel with minimal vessel trauma.

Another object of the invention is to provide a high-speed rotational atherectomy device having at least one flexible eccentric abrading and cutting head with proximal and/or distal radiused edges and that flexes during insertion and placement, providing an improved ability to navigate tortuous lumens with minimal trauma.

Another object of the invention is to provide a high-speed rotational atherectomy device having at least one non-flexible abrading and eccentric cutting head with proximal and/or distal radiused edges and that does not flex during placement or high-speed rotational operation.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1:
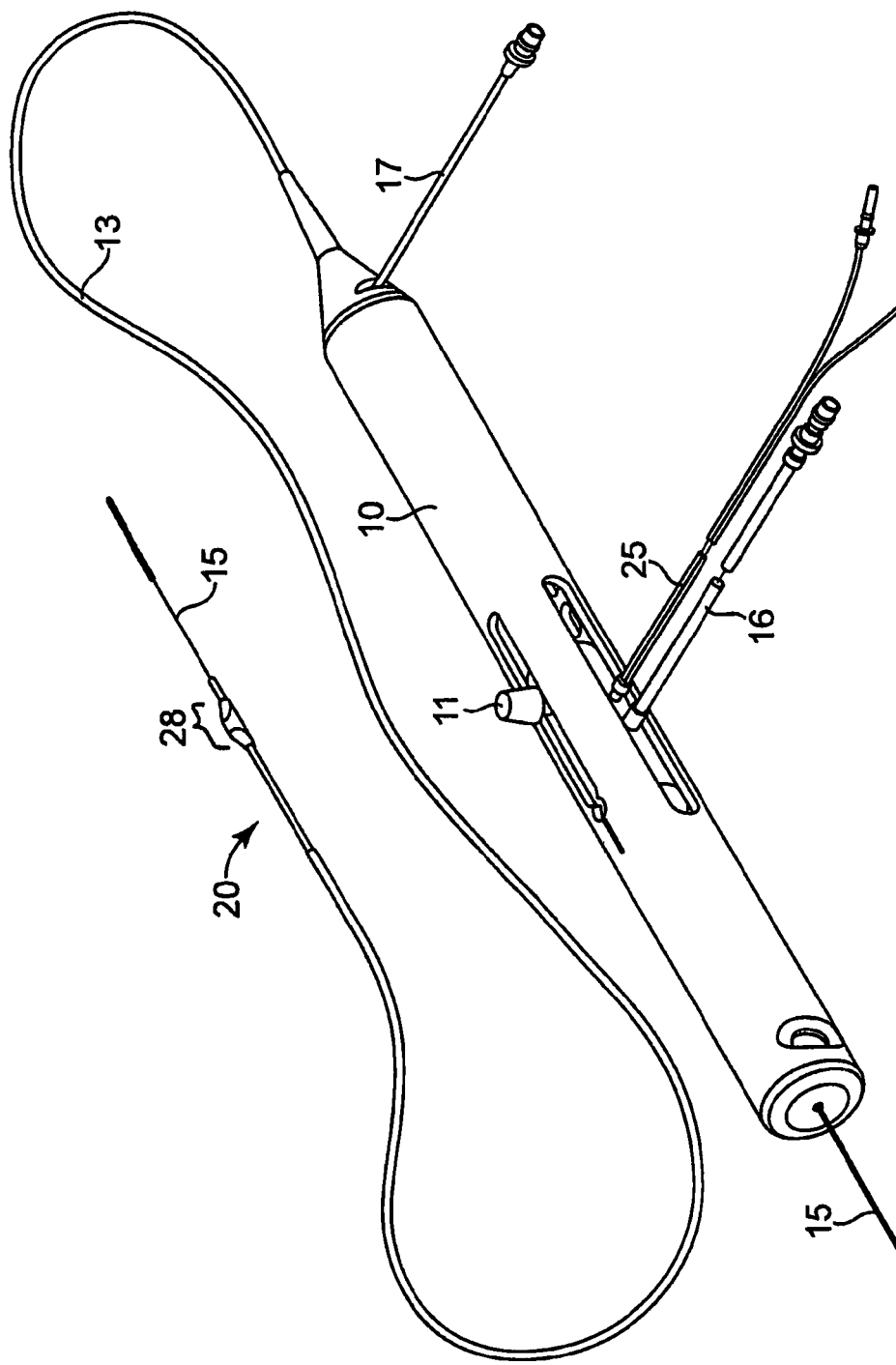
FIG. 1 is a perspective view of one embodiment of a rotational atherectomy device and system comprising one embodiment of the non-flexible eccentric cutting head of the invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

FIG. 1 illustrates one embodiment of a rotational atherectomy device according to the disclosure of commonly assigned U.S. patent application Ser. No. 11/761,128. The device includes a handle portion 10, an elongated, flexible drive shaft 20 having an eccentric enlarged abrading head 28, and an elongated catheter 13 extending distally from the handle portion 10. The drive shaft 20 is constructed from helically coiled wire as is known in the art and the abrading head 28 is fixedly attached thereto. Further to the various embodiments of the drive shaft that are contemplated by the present invention, the drive shaft's helically coiled wire may comprise as few as three wires or as many as 15 wires and may have a right hand or a left hand winding as will be known to the skilled artisan. The catheter 13 has a lumen in which most of the length of the drive shaft 20 is disposed, except for the enlarged abrading head 28 and a short section distal to the enlarged abrading head 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20 (details regarding such handles and associated instrumentation are well know in the industry, and are described, e.g., in U.S. Pat. No. 5,314,407, issued to Auth). The handle 10 also desirably includes a control knob 11 for advancing and retracting the turbine and drive shaft 20 with respect to the catheter 13 and the body of the handle.

Figure 2:
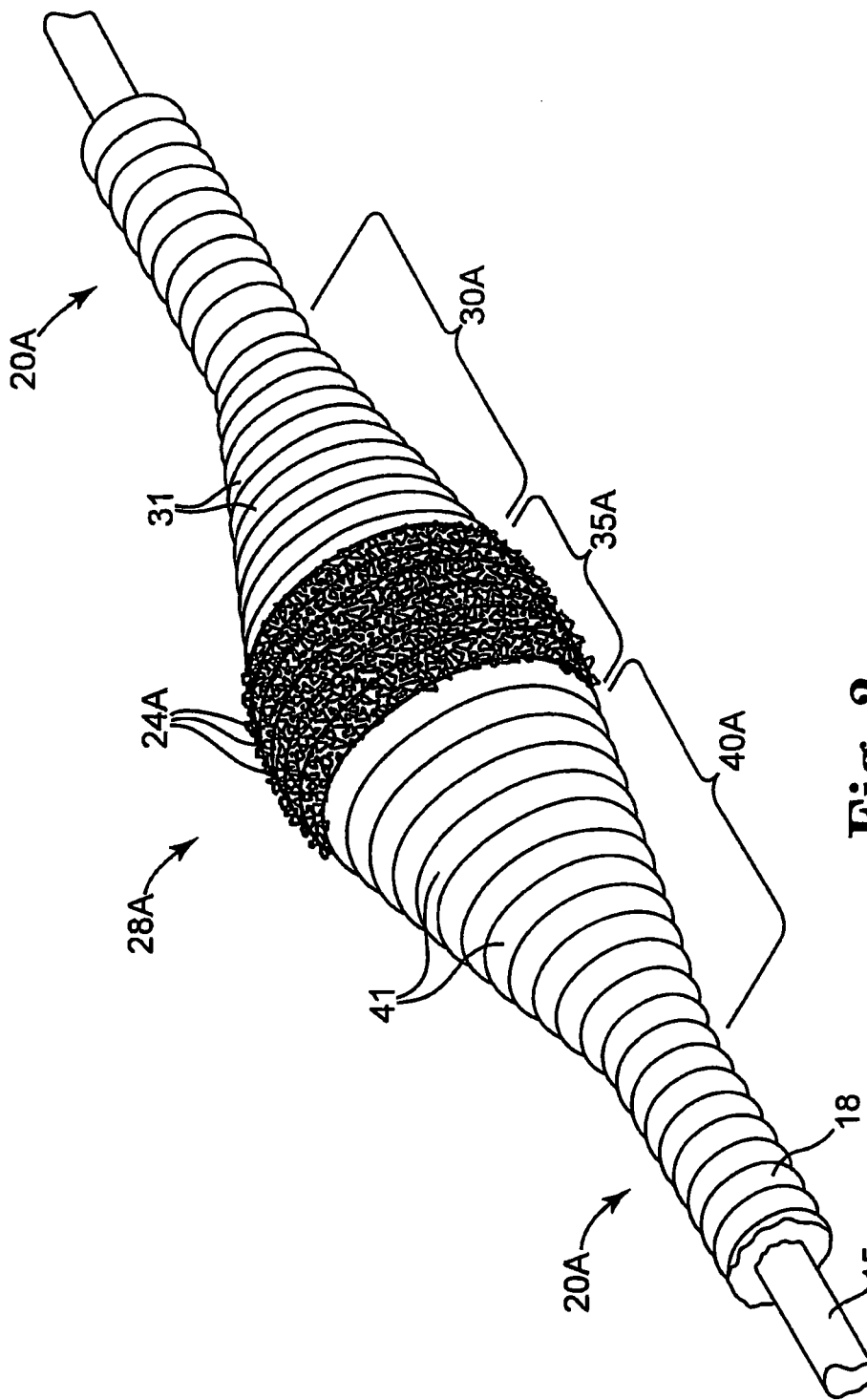
FIG. 2 is perspective, broken-away view of a prior art flexible eccentric cutting head formed from the drive shaft.
Figure 3:
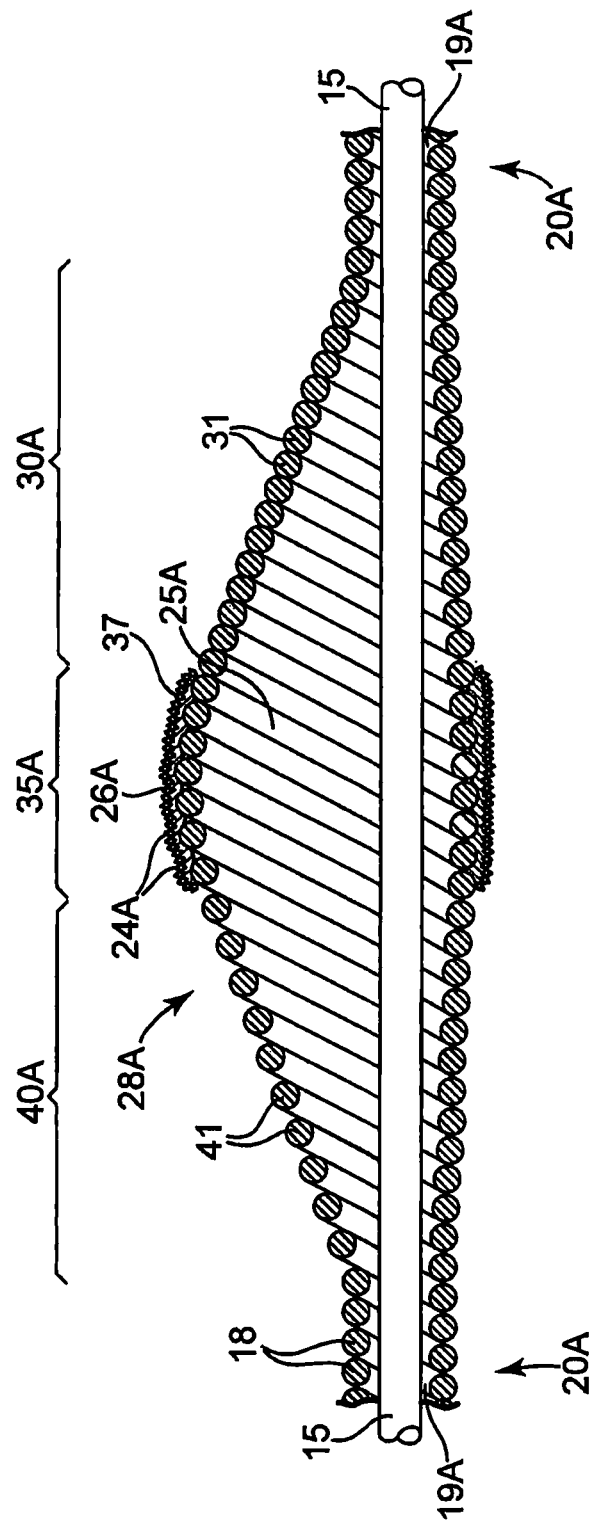
FIG. 3 is a broken-away, longitudinal cross-sectional view of a prior art eccentric cutting head formed from the drive shaft.
Figure 4:
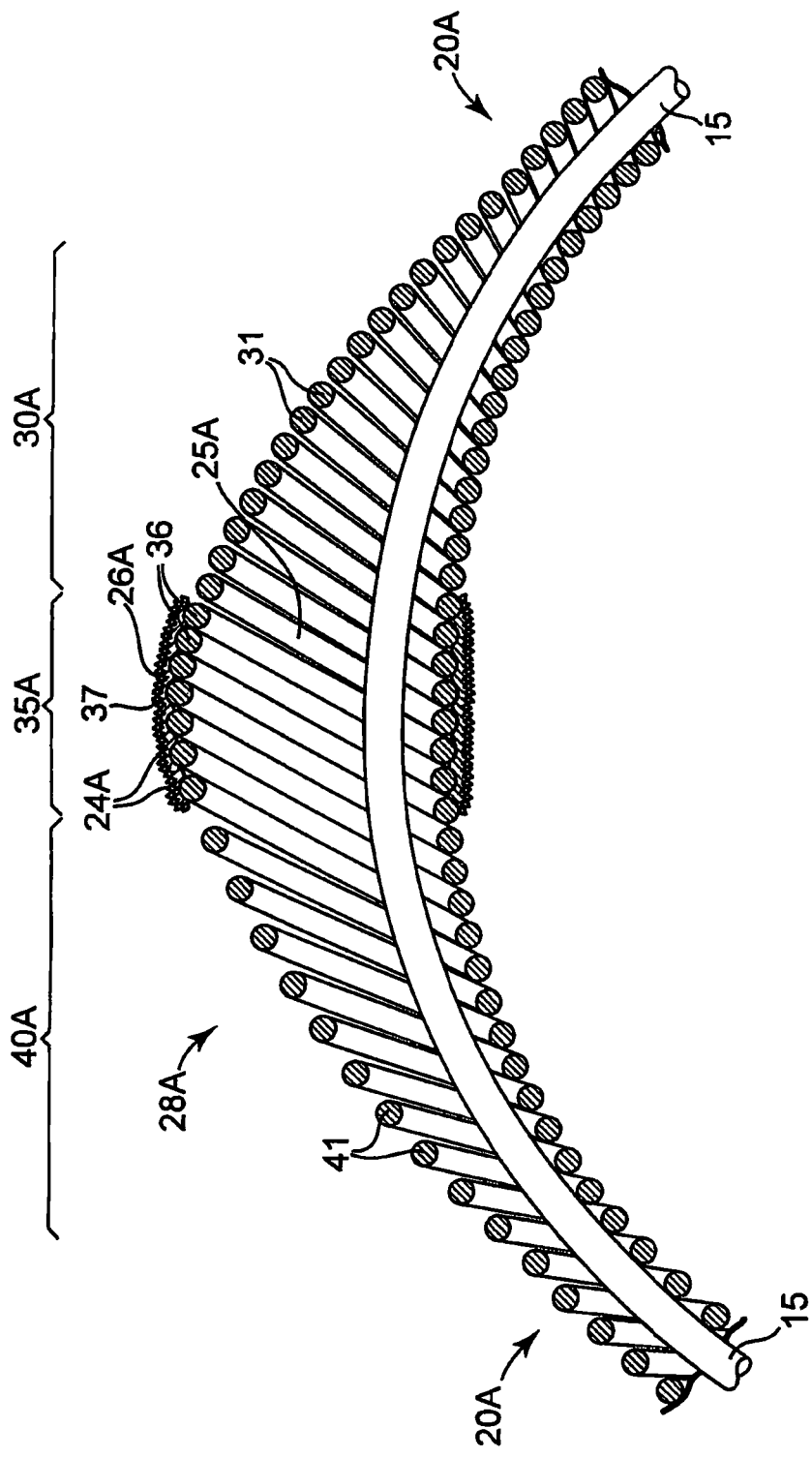
FIG. 4 is a broken-away, longitudinal cross-sectional view illustrating the flexibility of a prior art flexible eccentric enlarged cutting head formed from the drive shaft.

FIGS. 2-4 illustrate details of a prior art device comprising an eccentric enlarged diameter abrading section 28A of a drive shaft 20A. The drive shaft 20A comprises one or more helically wound wires 18 which define a guide wire lumen 19A and a hollow cavity 25A within the enlarged abrading section 28A. Except for the guide wire 15 traversing the hollow cavity 25A, the hollow cavity 25A is substantially empty. The eccentric enlarged diameter abrading section 28A includes, relative to the location of the stenosis, proximal 30A, intermediate 35A and distal 40A portions. Wire turns 31 of the proximal portion 30A of the eccentric enlarged diameter section 28A preferably have diameters that progressively increase distally at a generally constant rate, thereby forming generally the shape of a cone. Wire turns 41 of the distal portion 40A preferably have diameters that progressively decrease distally at a generally constant rate, thereby forming generally the shape of a cone. Wire turns 36 of the intermediate portion 35A are provided with gradually changing diameters to provide a generally convex outer surface which is shaped to provide a smooth transition between the proximal and distal conical portions of the enlarged eccentric diameter section 28A of the drive shaft 20A.

Continuing with the prior art device of FIGS. 2-4, at least part of the eccentric enlarged diameter abrading section of the drive shaft 28A (preferably the intermediate portion 35A) comprises an external surface capable of removing tissue. A tissue removing surface 37 comprising a coating of an abrasive material 24A to define a tissue removing segment of the drive shaft 20A is shown attached directly to the wire turns of the drive shaft 20A by a suitable binder 26A.

FIG. 4 illustrates the flexibility of the prior art eccentric enlarged diameter abrading section of the drive shaft 28A, shown with drive shaft 20A advanced over guide wire 15. In the embodiment shown, adjacent wire turns of the intermediate portion 35A of the eccentric enlarged cutting head of the drive shaft are secured to one another by the binding material 26A securing the abrasive particles 24A to the wire turns 36. Proximal portion 30A and distal 40A portion of the eccentric enlarged diameter section of the drive shaft comprise wire turns 31 and 41, respectively, are not secured to one another, thereby permitting such portions of the drive shaft to flex, as shown in the drawing. Such flexibility facilitates advancement of the device through relatively tortuous passageways and, in some embodiments, flexing of the eccentric enlarged diameter abrading section 28A during high-speed rotation. Alternatively, adjacent wire turns 36 of the intermediate portion 35A of the eccentric enlarged diameter abrading section 28A of the drive shaft may be secured to one another, thereby limiting the flexibility of abrading section 28A.

Figure 5:
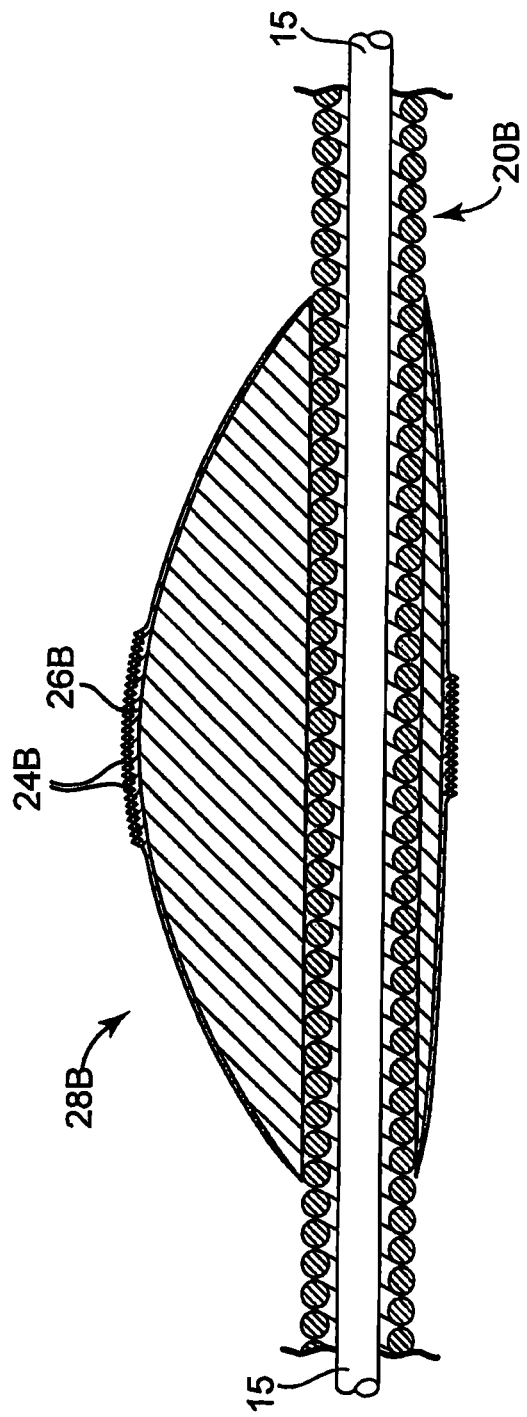
FIG. 5 is a longitudinal cross-sectional view of a prior art solid and inflexible eccentric abrasive burr attached to a drive shaft.

FIG. 5 illustrates another prior art rotational atherectomy device which employs a solid asymmetrical abrasive burr 28B attached to a flexible drive shaft 20B, rotated over a guide wire 15 such as provided by U.S. Pat. No. 5,681,336 to Clement. The drive shaft 20B may be flexible, however the solid asymmetrical abrasive burr 28B is inflexible. The eccentric tissue removing burr 28B has a coating of abrasive particles 24B secured to a portion of its outer surface by a suitable binding material 26B. This construction has limited utility, however because, as Clement explains at Col. 3, lines 53-55, the asymmetrical burr 28B must be rotated at "lower speeds than are used with high speed ablation devices, to compensate for heat or imbalance." That is, given both the size and mass of the solid burr-type construction, it is infeasible to rotate such a burr at the high speeds used during atherectomy procedures, i.e., 20,000-200,000 rpm. Essentially, the center of mass offset from the rotational axis of the drive shaft in this prior art device would result in development of significant centrifugal force, exerting too much pressure on the wall of the artery and creating too much heat, unnecessary trauma and excessively large particles.

Figure 6:
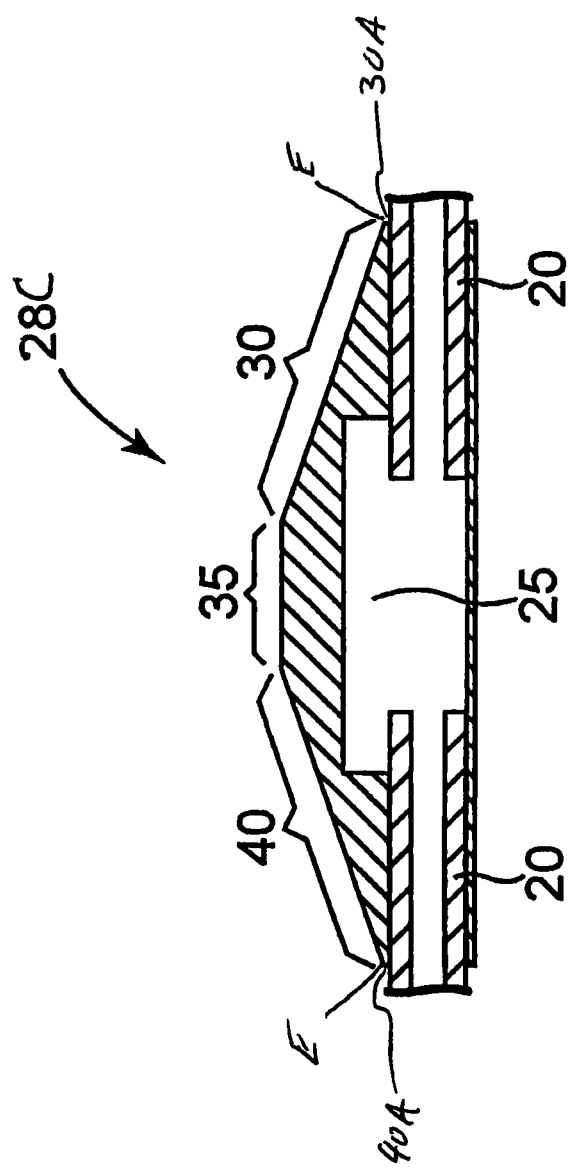
FIG. 6 is a broken-away longitudinal cross-sectional view of a prior art abrasive crown having sharp proximal and distal edges.

FIG. 6 illustrates further one embodiment of the eccentric enlarged abrading head 28C disclosed in commonly assigned U.S. patent application Ser. No. 11/761,128. In this embodiment, the drive shaft 20 is illustrated as attaching to the abrading head 28C in two separate sections, with a gap therebetween and the eccentric abrading head 28 attached to both drive shaft sections. Alternatively, the drive shaft 20 may be of single piece construction. A proximal portion 30 and the distal portion 40 are shown with substantially equivalent lengths with intermediate portion 35 interposed therebetween. Proximal leading edge 30A and distal leading edge 40A are illustrated as substantially perpendicular with drive shaft 20, thus forming hard and sharp edges E. Such hard and sharp edges may result in trauma to the vessel lining during high-speed rotation; a result that is highly undesireable.

Turning now to FIGS. 7-11, one embodiment of the non-flexible, eccentric enlarged abrading head 28 of the rotational atherectomy device of the invention will be discussed. The abrading head 28 may comprise at least one tissue removing surface 37 on the external surface(s) of the intermediate portion 35, the distal portion 40 and/or the proximal portion 30 to facilitate abrasion of the stenosis during high speed rotation. The tissue removing surface 37 may comprise a coating of an abrasive material 24 bound to the external surface(s) of the intermediate portion 35, the distal portion 40 and/or the proximal portion 30 of abrading head 28. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the tissue removing surface(s) by a suitable binder—such attachment may be achieved using well known techniques, such as conventional electroplating or fusion technologies (see, e.g., U.S. Pat. No. 4,018,576). Alternately the external tissue removing surface may comprise mechanically or chemically roughening the external surface(s) of the intermediate portion 35, the distal portion 40 and/or the proximal portion 30 to provide a suitable abrasive tissue removing surface 37. In yet another variation, the external surface may be etched or cut (e.g., with a laser) to provide small but effective abrading surfaces. Other similar techniques may also be utilized to provide a suitable tissue removing surface 37.

Figure 9:
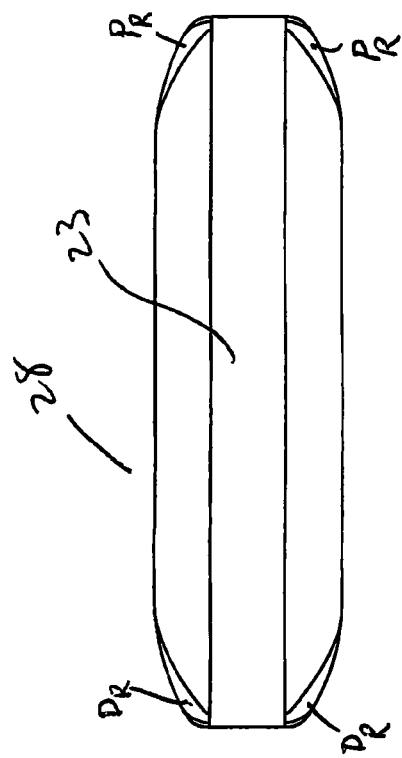
FIG. 9 is a bottom view of one embodiment of the present invention.
Figure 10:
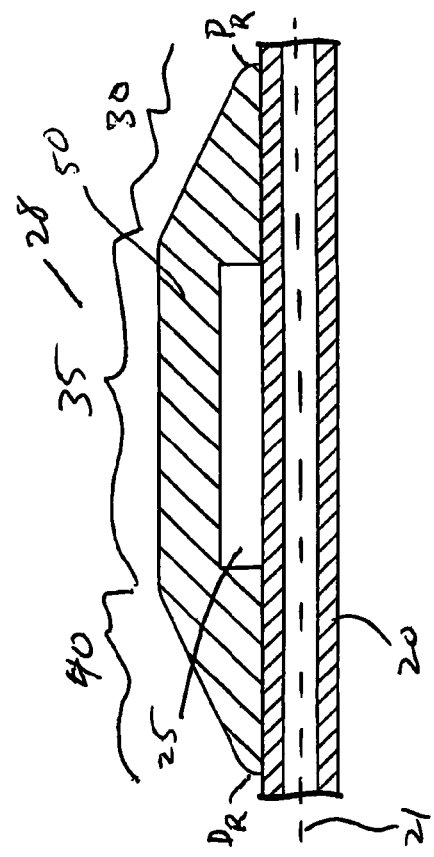
FIG. 10 is a broken away cross-sectional view of one embodiment of the present invention.
Figure 7:
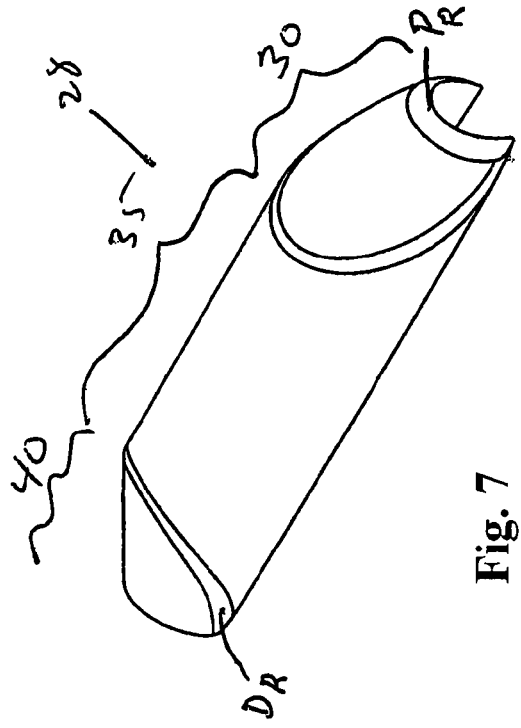
FIG. 7 is a perspective view of one embodiment of the present invention.
Figure 8:
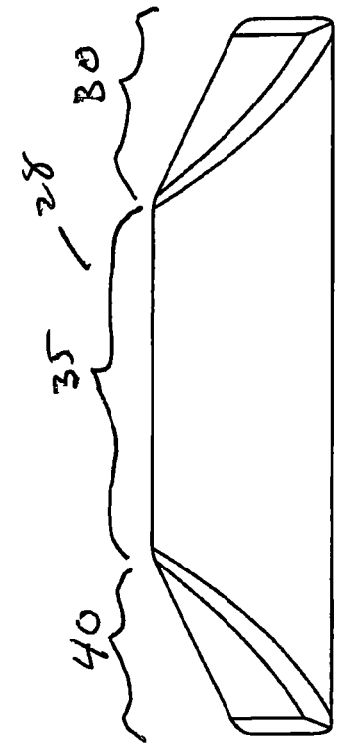
FIG. 8 is a side view of one embodiment of the present invention.

As best illustrated in FIGS. 9 and 10, an at least partially enclosed lumen or slot 23 may be provided longitudinally through the enlarged abrading head 28 along the rotational axis 21 of the drive shaft 20 for securing the abrading head 28 to the drive shaft 20 in a manner well known to those skilled in the art. In various embodiments, a hollowed chamber 25 may be provided to lessen and manipulate the mass (and center of mass location relative to the drive shaft rotational axis 21) of the abrading head 28 to facilitate atraumatic abrasion and improve predictability of control of the orbital pathway of the abrading head 28 during high speed, i.e., 20,000 to 200,000 rpm, operation. As those skilled in the art will recognize, the orbital amplitude will be predictably manipulated based upon the positioning of the center of mass in relation to the rotational axis of the drive shaft. Thus, a larger hollowed chamber 25 will work to move the center of mass closer to the rotational axis 21 than will a smaller hollowed chamber 25 (or no hollowed chamber 25) and, at a given rotational speed, will create a smaller orbital amplitude and/or diameter for the abrading head 28 during high-speed rotation.

Each of the FIGS. 7-11 illustrate the radiused proximal and distal edges $P_R$, $D_R$. The rounded nature of the proximal edges $P_R$, $D_R$ facilitate gradual entry into a stenosis while minimizing any collateral trauma to the vessel lining. There are any number of radii possible for the distal and/or proximal edges $P_R$, $D_R$ as those skilled in the art will readily recognize; the entire range of such radii are within the scope of the present invention. The embodiment illustrated in the Figures comprise radiused edges that are of equivalent radius, however the proximal and/or distal edges $P_R$, $D_R$ may comprise radii that are not equivalent. Moreover, in alternate embodiments, the abrading head may comprise a proximal radiused edge while the distal end surface is not radiused. Still more alternatively, the distal edge may be radiused while the proximal end surface is not.

In the illustrated embodiment, the abrading head 28 may be fixedly attached to the drive shaft 20, wherein the drive shaft comprises one single unit. Alternatively, as will be discussed below, the drive shaft 20 may comprise two separate pieces, wherein the enlarged eccentric abrading head 28 is fixedly attached to both drive shaft 20 pieces, with a gap therebetween. This two-piece drive shaft construction technique may, in combination with hollowed chamber 25, allow further manipulation of the placement of the center of mass of the abrading head 28. The size and shape of the hollowed chamber 25 may be modified to optimize the orbital rotational path of the abrading head 28 for particularly desirable rotational speeds. Those skilled in the art will readily recognize the various possible configurations, each of which is within the scope of the present invention.

The embodiment of FIGS. 7-11 illustrates the proximal portion 30 and distal portion 40 of symmetrical shape and length. Alternate embodiments may increase the length of either the proximal portion 30 or the distal portion 40, to create an asymmetrical longitudinal profile.

Figure 11:
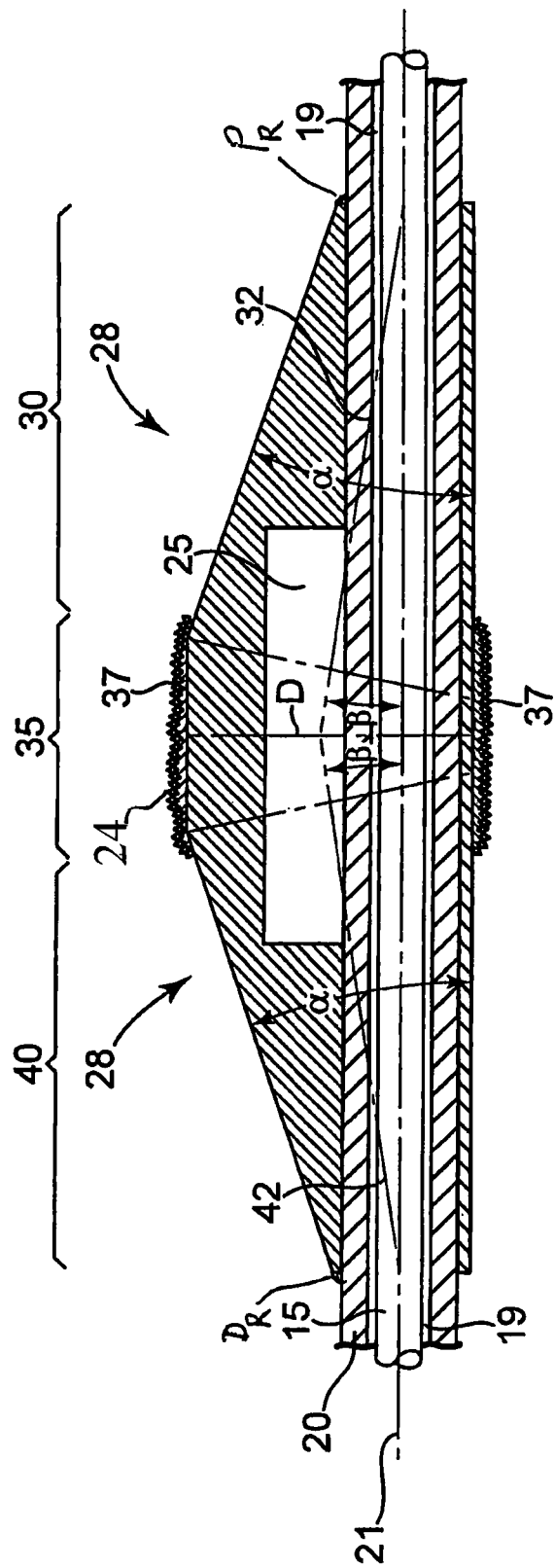
FIG. 11 is a broken-away, longitudinal cross-sectional view illustrating the geometry of one embodiment of the present invention.

Specifically with reference to FIG. 11, the drive shaft 20 has a rotational axis 21 which is coaxial with the guide wire 15, the guide wire 15 being disposed within the lumen 19 of the drive shaft 20. Thus, the proximal portion 30 of the eccentric enlarged abrading head 28 has an outer surface which is substantially defined by the lateral surface of a frustum of a cone, the cone having an axis 32 which intersects the rotational axis 21 of the drive shaft 20 at a relatively shallow angle $\beta$. Similarly, the distal portion 40 of the enlarged abrading head 28 has an outer surface which is substantially defined by the lateral surface of a frustum of a cone, the cone having an axis 42 which also intersects the rotational axis 21 of the drive shaft 20 at a relatively shallow angle $\beta$. The cone axis 32 of the proximal portion 30 and the cone axis 42 of the distal portion 40 intersect each other and are coplanar with the longitudinal rotational axis 21 of the drive shaft.

The opposing sides of the cones generally should be at an angle $\alpha$ of between about 10° and about 30° with respect to each other; preferably the angle $\alpha$ is between about 20° and about 24°, and most preferably the angle $\alpha$ is about 22°. Also, the cone axis 32 of the proximal portion 30 and the cone axis 42 of the distal portion 40 normally intersect the rotational axis 21 of the drive shaft 20 at an angle $\beta$ of between about 20° and about 8°. Preferably the angle $\beta$ is between about 3° and about 6°. Although in the preferred embodiment shown in the drawings the angles $\alpha$ of the distal and proximal portions of the enlarged abrading head 28 are generally equal, they need not be equal. The same is true for the angles $\beta$.

In an alternate embodiment, the intermediate portion 35 may comprise a diameter that gradually increases from the intersection with the distal portion 40 to the intersection of the proximal portion 30. In this embodiment, angle $\alpha$, as illustrated in FIG. 6, may be larger in the proximal portion 30 than the distal portion 40, or vice versa. Further alternate embodiments comprise the intermediate portion 35 having a surface that is convex, wherein the intermediate portion outer surface may be shaped to provide a smooth transition between the proximal and distal outer surfaces of the proximal and distal portions.

Because the cone axes 32 and 42 intersect the rotational axis 21 of the drive shaft 20 at an angle $\beta$ the eccentric enlarged abrading head 28 has a center of mass that is spaced radially away from the longitudinal rotational axis 21 of the drive shaft 20. As will be described in greater detail below, offsetting the center of mass from the drive shaft's axis of rotation 21 provides the enlarged abrading head 28 with an eccentricity that permits it to open an artery to a diameter substantially larger, than the nominal diameter of the enlarged eccentric abrading head 28, preferably the opened diameter is at least twice as large as the nominal resting diameter of the enlarged eccentric abrading head 28.

Figure 12C:
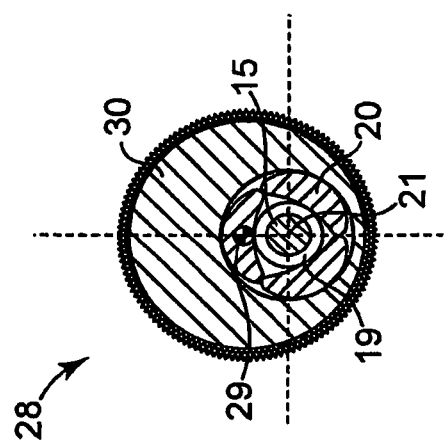
FIGS. 12A-12C are transverse cross-sectional views of one embodiment of the eccentric cutting head of the invention.
Figure 12B:
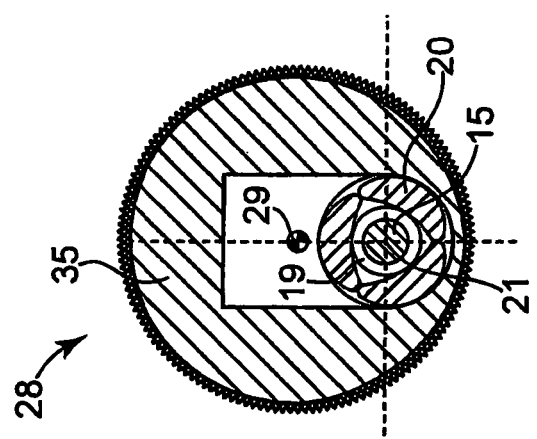
Figure 12A:
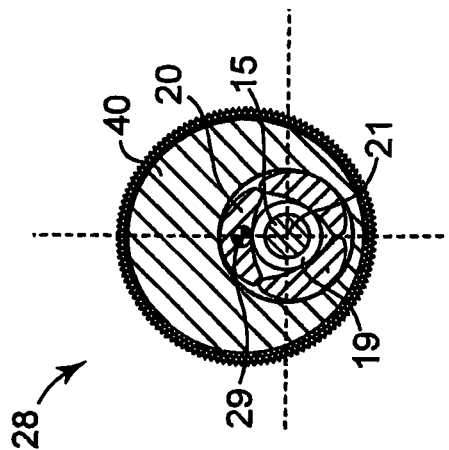

FIGS. 12A-12C depict the positions of the centers of mass 29 of three cross-sectional slices (shown as faces of transverse cross-sections) of the eccentric enlarged abrading head 28 shown in FIGS. 7-11, with the eccentric enlarged abrading head 28 fixedly attached to the drive shaft 20, the drive shaft 20 advanced over guide wire 15, the guide wire 15 within drive shaft lumen 19. The entire eccentric enlarged abrading head 28 may be divided into many such thin slices, each slice having its own center of mass. FIG. 12B is taken at a position where the eccentric enlarged abrading head 28 has its maximum cross-sectional diameter (which, in this embodiment, is the maximum diameter of the intermediate portion 35 of the eccentric enlarged abrading head 28), and FIGS. 12A and 12C are cross-sections, respectively, of the distal 40 and proximal 30 portions of the eccentric enlarged abrading head 28. In each of these cross-sectional slices the center of mass 29 is spaced away from the rotational axis 21 of the drive shaft 20, the rotational axis of the drive shaft 20 coinciding with the center of the guide wire 15. The center of mass 29 of each cross-sectional slice also generally coincides with the geometric center of such cross-sectional slice. FIG. 12B illustrates the cross sectional slice of intermediate portion 35, comprising the largest cross-sectional diameter of abrading head 28, wherein both the center of mass 29 and the geometric center are located the furthest (i.e., maximally spaced away) from the rotational axis 21 of the drive shaft 20 compared with proximal 30 and distal 40 portions.

It should be understood that, as used herein, the word "eccentric" is defined and used herein to refer to either a difference in location between the geometric center of the enlarged abrading head 28 and the rotational axis 21 of the drive shaft 20, or to a difference in location between the center of mass 29 of the enlarged abrading head 28 and the rotational axis 21 of the drive shaft 20. Either such difference, at the proper rotational speeds, will enable the eccentric enlarged abrading head 28 to open a stenosis to a diameter substantially greater than the nominal diameter of the eccentric enlarged abrading head 28. Moreover, for an eccentric enlarged abrading head 28 having a shape that is not a regular geometric shape, the concept of "geometric center" can be approximated by locating the mid-point of the longest chord which is drawn through the rotational axis 21 of the drive shaft 28 and connects two points on a perimeter of a transverse cross-section taken at a position where the perimeter of the eccentric enlarged abrading head 28 has its maximum length.

The abrading head 28 of the rotational atherectomy device of the invention may be constructed of stainless steel, tungsten or similar material. The abrading head 28 may be a single piece unitary construction or, alternatively, may be an assembly of two or more abrading head components fitted and fixed together to achieve the objects of the present invention.

Those skilled in the art will recognize that the embodiments illustrated herein, including may comprise at least one tissue removing surface 37 as described above. This tissue removing surface 37 may be disposed on one or more of the intermediate portion 35, proximal portion 30 and/or distal portion 40 of the eccentric abrading head 28. The proximal and/or distal radiused edges $P_R$, $D_R$ may also comprise a tissue removing surface with an abrasive material disposed thereon as described herein.

In certain situations, including the one presently under discussion, the abrading head 28 may be used to gradually and atraumatically create an opening using the increasing diameter of the distal portion 40 of the abrading head 28 to increase the diameter of the opening until sufficient plaque has been removed to allow advancement of the abrading head 28 through and across the stenosis and then retraction thereof.

The ability to create pilot holes is enhanced by several features. The cone-shaped proximal portion 30 allows gradual advancement and controlled abrading access of the tissue removing surface 37 to the stenosis, creating a pilot hole for the continued advancement of the abrading head 28. The rounded radiused proximal and/or distal edges $P_R$, $D_R$ further facilitate creation of a pilot hole and may, as described herein, comprise an abrasive material and surface thereon to help gradually and atraumatically open a pilot hole. Further, the intersections of the cone-shaped proximal portion 30 (and distal portion 40—not shown in the figure) with the cylinder-shaped intermediate portion 35 of the abrading head 28 may define edges with an ability to cut or abrade plaque as the device is gradually advanced, thus increasing the diameter of the abraded stenosis. Moreover, as discussed above, the surfaces of the proximal portion 30, as well as the intermediate 35 and distal portions 40 (not shown in the figure) of the abrading head 28 may be covered in whole or in part with the abrasive material of the tissue removing surface 37, thus facilitating plaque abrasion and opening of the stenosis in a gradual and controlled manner during advancement and retraction through the stenosis. Ultimately, sufficient plaque will be removed to allow the entire abrading head 28 may be advanced across the stenosis and retracted.

In addition, the non-flexible abrading head 28 may be sized appropriately for the creation of pilot holes through a stenosis, essentially creating access for successively larger abrading head(s) 28 of the present invention to follow so that the opening is opened gradually, or perhaps creates a pilot hole to allow subsequent access by certain prior art devices such as that described in Shturman U.S. Pat. No. 6,494,890, i.e., the flexible eccentric enlarged section of the drive shaft. Such an arrangement may comprise using two separate devices or combining the two (or more) within one device. For example, it may be advantageous to place a non-flexible eccentric abrading head 28 of the present invention distally along the drive shaft 20 in combination with a more proximally placed flexible eccentric enlarged abrading section of the drive shaft 20 as disclosed in Shturman '890. In this embodiment, a pilot hole may be opened using the non-flexible abrading head 28, so that the flexible eccentric enlarged abrading section of the drive shaft 20 may follow through the stenosis, opening it still further. Alternatively, successively larger non-flexible abrading heads 28 may be placed in series along the drive shaft 20, the smallest being most distal along the drive shaft 20, i.e., most proximal to the stenosis. Still more alternatively, a combination of non-flexible and flexible (discussed infra), eccentric abrading heads 28 may be provided in series along the drive shaft 20.

Figure 13:
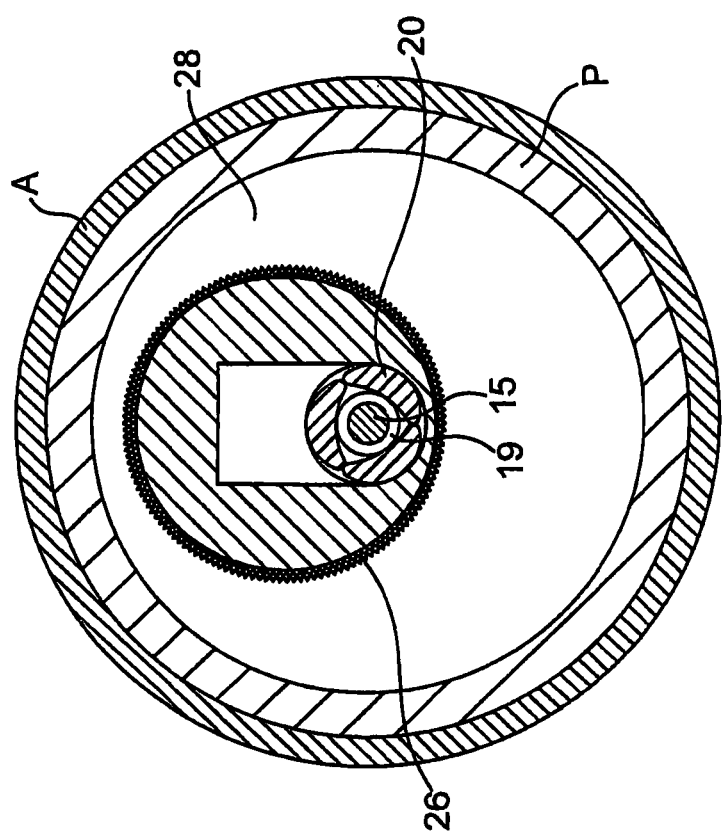
FIG. 13 is a longitudinal cross-sectional view showing one embodiment of the cutting head of the invention in an at-rest (non-rotating) position after a stenosis has been substantially opened by the device.

FIG. 13 depicts the enlarged eccentric abrading head 28 of the present invention with drive shaft 20 and the attached abrading head 28 advanced over guide wire 15 and in an "at-rest" position within the artery "A", after the stenosis has been substantially opened, thus illustrating the device's ability to open a stenosis to a diameter well in excess of the device's nominal diameter.

The extent to which a stenosis in an artery can be opened to a diameter larger than the nominal diameter of the eccentric enlarged abrading head of the present invention depends on several parameters, including the shape of the eccentric enlarged abrading head, the mass of the eccentric enlarged abrading head, the distribution of that mass and, therefore, the location of the center of mass within the abrading head with respect to the rotational axis of the drive shaft, and the speed of rotation.

The speed of rotation is a significant factor in determining the centrifugal force with which the tissue removing surface of the enlarged abrading head is pressed against the stenotic tissue, thereby permitting the operator to control the rate of tissue removal. Control of the rotational speed also allows, to some extent, control over the maximum diameter to which the device will open a stenosis. Applicants have also found that the ability to reliably control the force with which the tissue removing surface is pressed against the stenotic tissue not only permits the operator to better control the rate of tissue removal but also provides better control of the size of the particles being removed.

Figure 14:
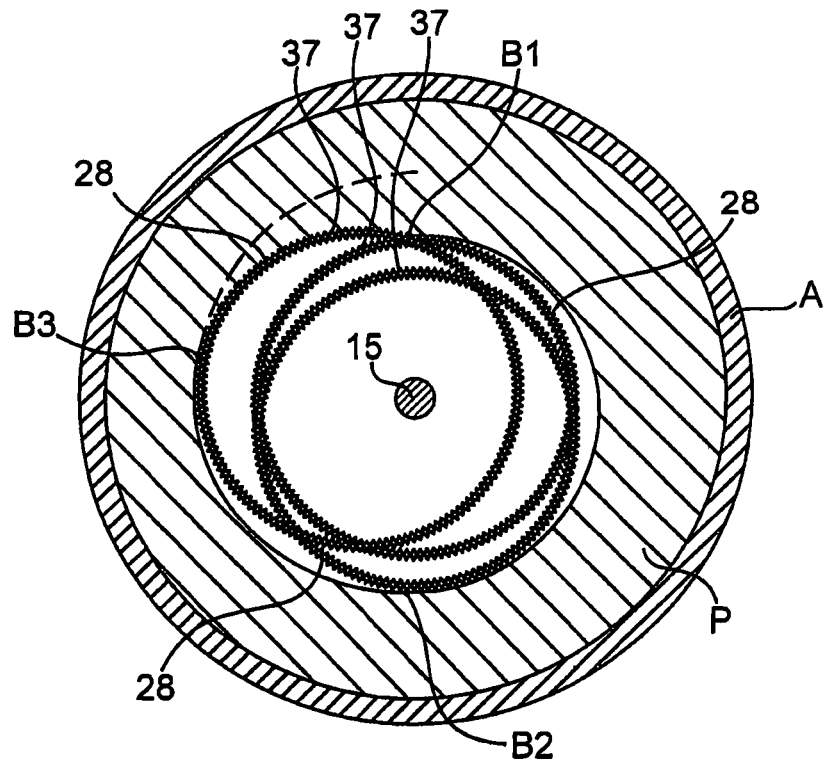
FIG. 14 is a transverse cross-sectional view illustrating three different positions of the rapidly rotating eccentric enlarged cutting head of an eccentric rotational atherectomy device of the invention.
Figure 15:
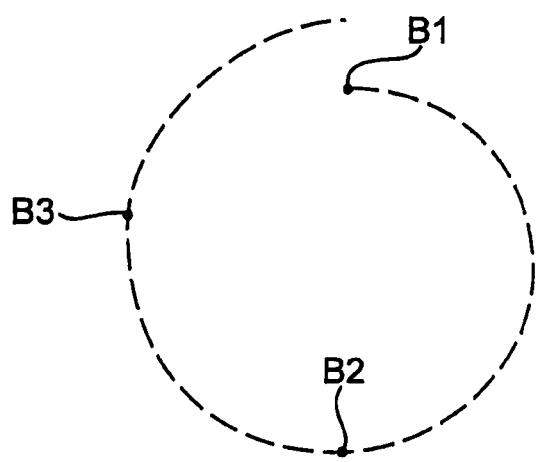
FIG. 15 is a schematic diagram illustrating the three different positions of the rapidly rotating eccentric enlarged cutting head of an eccentric rotational atherectomy device of the invention shown in FIG. 14.

FIGS. 14-15 illustrate the generally spiral orbital path taken by various embodiments of the eccentric abrading head 28 of the present invention, the abrading head 28 shown relative to the guide wire 15 over which the abrading head 28 has been advanced. The pitch of the spiral path in FIG. 14-15 is exaggerated for illustrative purposes—in reality, each spiral path of the eccentric enlarged abrading head 28 removes only a very thin layer of tissue via the tissue removing surface 37, and many, many such spiral passes are made by the eccentric enlarged abrading head 28 as the device is repeatedly moved forward and backward across the stenosis to fully open the stenosis. FIG. 14 shows schematically three different rotational positions of the eccentric enlarged abrading head 28 of a rotational atherectomy device of the invention. At each position the abrasive surface of the eccentric enlarged abrading head 28 contacts the plaque "P" to be removed—the three positions are identified by three different points of contact with the plaque "P", those points being designated in the drawing as points B1, B2, and B3. Notice that at each point it is generally the same portion of the abrasive surface of the eccentric enlarged abrading head 28 that contacts the tissue— the portion of the tissue removing surface 37 that is radially most distant from the rotational axis of the drive shaft.

In addition to the non-flexible abrading head embodiments described above, various embodiments of the present invention further comprise some flexibility in the eccentric abrading head 28. Exemplary embodiments are illustrated in FIG. 16.

Figure 16:
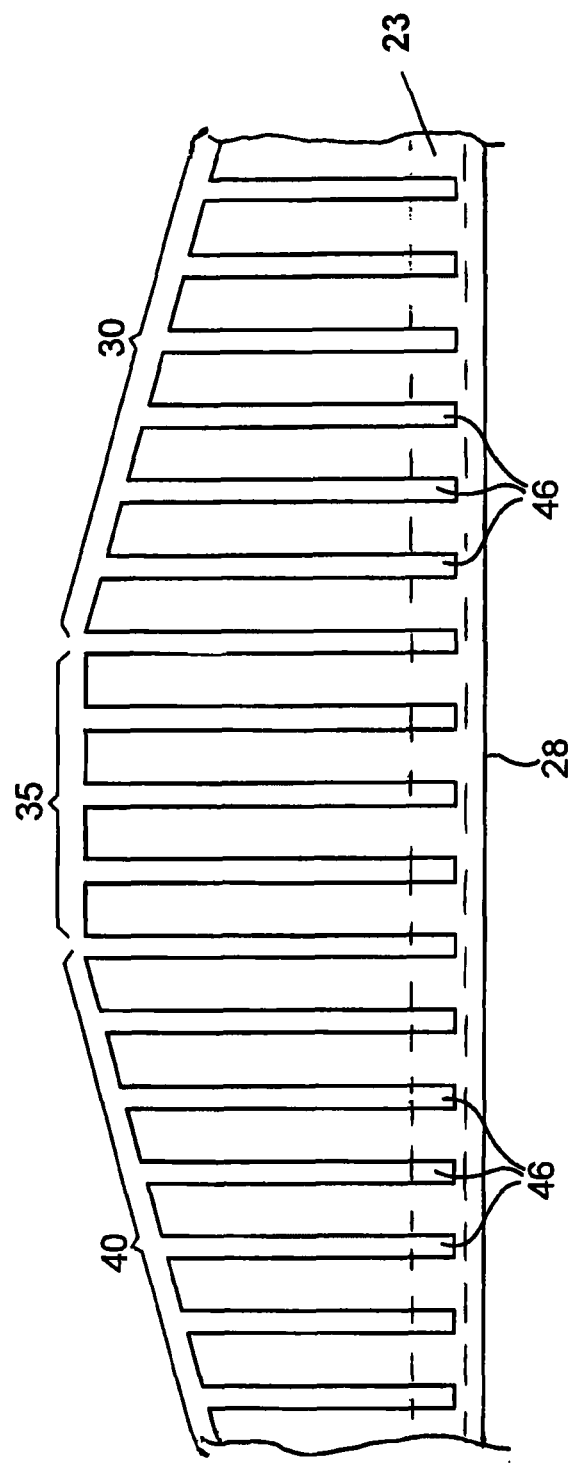
FIG. 16 is a broken away side view of one embodiment of the present invention with flexibility slots integrated therein.

FIG. 16 illustrates an abrading head similar to that provided in FIGS. 7-11 but with flexibility slots 46 being disposed on the abrading head 28. The slots 46 are illustrated as being cut completely through the abrading head 28 and into lumen 23 to allow for maximum flex of the abrading head 28. However, the skilled artisan will recognize that the slots 46 need not extend into lumen 23 and may instead achieve flexibility by in effect scoring the abrading head 28 but not extending into lumen 23. In various embodiments, abrading head 28 will flex with the flexible drive shaft 20 to ease negotiation of tortuous passageways within the subject lumen. Such flexibility in the abrading head 28 thus may provides a less traumatic entry enroute to the lesion to be abraded as well as a less traumatic exit therefrom. At least one flexibility slot 46 is required to provide such flexibility; preferably a plurality of flexibility slots 46 will be provided.

The embodiment of the flexible abrading head 28 of FIG. 16 illustrates a series of evenly placed flexibility slots 46 of substantially consistent width and depth wherein the slots 46 are cut completely through the abrading head 28 to the lumen 23 therein. Those skilled in the art will recognize that the flexibility of the abrading head 28 may be controlled, i.e., modified, through manipulation of, inter alia, one or more of the following elements: number of slots 46; depth of slots 46 within abrading head 28; width of slots 46; angle of cut of slots 46; placement of the slots 46 on the abrading head 28.

Thus, the flexibility characteristics of the abrading head may be controlled or modified using flexibility slots 46. Certain embodiments of the present invention may comprise, e.g., flexibility slots 46 concentrated near the center of the abrading head 28, i.e., arranged within the intermediate portion 35, with only one slot 46 engaging the proximal portion 30 and only one slot 46 engaging the distal portion 40. It will be obvious to the skilled artisan that many equivalents are possible; each of which are within the scope of the present invention.

Each of the flexible abrading head embodiments may comprise abrasive material disposed thereon as discussed above in connection with the non-flexible embodiments.

Thus the eccentric abrading head 28 of the present invention may comprise non-flexible and/or at least partially flexible embodiments.

Although not wishing to be constrained to any particular theory of operation, applicants believe that offsetting the center of mass from the axis of rotation produces an "orbital" movement of the enlarged abrading head, the diameter of the "orbit" being controllable by varying, inter alia, the rotational speed of the drive shaft. Whether or not the "orbital" movement is as geometrically regular as is shown in FIGS. 14-15 has not been determined, but applicants have empirically demonstrated that by varying the rotational speed of the drive shaft one can control the centrifugal force urging the tissue removing surface of the eccentric enlarged abrading head 28 against the surface of the stenosis. The centrifugal force can be determined according to the formula:

$$F_c = m \, \Delta x (\pi n/30)^2$$

where $F_c$ is the centrifugal force, m is the mass of the eccentric enlarged abrading head, $\Delta x$ is the distance between the center of mass of the eccentric enlarged abrading head and the rotational axis of the drive shaft, and n is the rotational speed in revolutions per minute (rpm). Controlling this force $F_c$ provides control over the rapidity with which tissue is removed, control over the maximum diameter to which the device will open a stenosis, and improved control over the particle size of the tissue being removed.

The abrading head 28 of the present invention comprises more mass than prior art high speed atherectomy abrading devices. As a result, a larger orbit may be achieved during high speed rotation which, in turn, allows for use of a smaller abrading head than with prior art devices. In addition to allowing for the creation of pilot holes in completely or substantially blocked arteries and the like, using a smaller abrading head will allow for greater ease of access and less trauma during insertion.

Operationally, using the rotational atherectomy device of the invention the eccentric enlarged abrading head 28 is repeatedly moved distally and proximally through the stenosis. By changing the rotational speed of the device he or she is able to control the force with which the tissue removal surface is pressed against the stenotic tissue, thereby being able to better control the speed of the plaque removal as well as the particle size of tissue removed. Since the stenosis is being opened to a diameter larger than the nominal diameter of the enlarged eccentric abrading head 28, the cooling solution and the blood are able to constantly flow around the enlarged abrading head. Such constant flow of blood and cooling solution constantly flushes away removed tissue particles, thus providing uniform release of removed particles, once the abrading head has passed through the lesion once.

The eccentric enlarged abrading head 28 may comprise a maximum cross-sectional diameter ranging between about 1.0 mm to about 3.0 mm. Thus, the eccentric enlarged abrading head may comprise cross-sectional diameters including, but not limited to: 1.0 mm, 1.25 mm, 1.50 mm, 1.75 mm, 2.0 mm, 2.25 mm, 2.50 mm, 2.75 mm, and 3.0 mm. Those skilled in the art will readily recognize that the incremental increases of 0.25 mm within the above-listing of cross-sectional diameter are exemplary only, the present invention is not limited by the exemplary listing and, as a result, other incremental increases in cross-sectional diameter are possible and within the scope of the present invention.

Because, as described above, the eccentricity of the enlarged abrading head 28 is dependent on a number of parameters, applicants have found that the following design parameters may be considered regarding the distance between the rotational axis 21 of the drive shaft 20 and the geometric center of a face of a transverse cross-section, taken at a position of maximum cross-sectional diameter of the eccentric enlarged abrading head: for a device having an eccentric enlarged abrading head with a maximum cross-sectional diameter between about 1.0 mm and about 1.5 mm, desirably the geometric center should be spaced away from the rotational axis of the drive shaft by a distance of at least about 0.02 mm, and preferably by a distance of at least about 0.035 mm; for a device having an eccentric enlarged abrading head with a maximum cross-sectional diameter between about 1.5 mm and about 1.75 mm, desirably the geometric center should be spaced away from the rotational axis of the drive shaft by a distance of at least about 0.05 mm, preferably by a distance of at least about 0.07 mm, and most preferably by a distance of at least about 0.09 mm; for a device having an eccentric enlarged abrading head with a maximum cross-sectional diameter between about 1.75 mm and about 2.0 mm, desirably the geometric center should be spaced away from the rotational axis of the drive shaft by a distance of at least about 0.1 mm, preferably by a distance of at least about 0.15 mm, and most preferably by a distance of at least about 0.2 mm; and for a device having an eccentric enlarged abrading head with a maximum cross-sectional diameter above 2.0 mm, desirably the geometric center should be spaced away from the rotational axis of the drive shaft by a distance of at least about 0.15 mm, preferably by a distance of at least about 0.25 mm, and most preferably by a distance of at least about 0.3 mm.

Design parameters can also be based on the location of the center of mass. For a device having an eccentric enlarged abrading head 28 with a maximum cross-sectional diameter between about 1.0 mm and about 1.5 mm, desirably the center of mass should be spaced away from the rotational axis of the drive shaft by a distance of at least about 0.013 mm, and preferably by a distance of at least about 0.02 mm; for a device having an eccentric enlarged abrading head 28 with a maximum cross-sectional diameter between about 1.5 mm and about 1.75 mm, desirably the center of mass should be spaced away from the rotational axis of the drive shaft by a distance of at least about 0.03 mm, and preferably by a distance of at least about 0.05 mm; for a device having an eccentric enlarged abrading head with a maximum cross-sectional diameter between about 1.75 mm and about 2.0 mm, desirably the center of mass should be spaced away from the rotational axis of the drive shaft by a distance of at least about 0.06 mm, and preferably by a distance of at least about 0.1 mm; and for a device having an eccentric enlarged abrading head with a maximum cross-sectional diameter above 2.0 mm, desirably the center of mass should be spaced away from the rotational axis of the drive shaft by a distance of at least about 0.1 mm, and preferably by a distance of at least about 0.16 mm.

Preferably, the thickness of the wall 50, e.g., as illustrated in FIG. 10, separating the hollow chamber from the outer surfaces defined by the proximal 30, intermediate 35 and/or distal 40 portions should be a minimum of 0.008 inches thick to preserve stability and integrity of the structure.

Preferably the design parameters are selected so that the enlarged abrading head 28 is sufficiently eccentric that, when rotated over a stationary guide wire 15 (held sufficiently taut so as to preclude any substantial movement of the guide wire) at a rotational speed greater than about 20,000 rpm, at least a portion of its tissue removing surface 37 may rotate through a path (whether or not such path is perfectly regular or circular) having a diameter larger than the maximum nominal diameter of the eccentric enlarged abrading head 28. For example, and without limitation, for an enlarged abrading head 28 having a maximum diameter between about 1.5 mm and about 1.75 mm, at least a portion of the tissue removal surface 37 may rotate through a path having a diameter at least about 10% larger than the maximum nominal diameter of the eccentric enlarged abrading head 28, preferably at least about 15% larger than the maximum nominal diameter of the eccentric enlarged abrading head 28, and most preferably at least about 20% larger than the maximum nominal diameter of the eccentric enlarged abrading head 28. For an enlarged abrading head having a maximum diameter between about 1.75 mm and about 2.0 mm, at least a portion of the tissue removal section may rotate through a path having a diameter at least about 20% larger than the maximum nominal diameter of the eccentric enlarged abrading head 28, preferably at least about 25% larger than the maximum nominal diameter of the eccentric enlarged abrading head 28, and most preferably at least about 30% larger than the maximum nominal diameter of the eccentric enlarged abrading head 28. For an enlarged abrading head 28 having a maximum diameter of at least about 2.0 mm, at least a portion of the tissue removal surface 37 may rotate through a path having a diameter at least about 30% larger than the maximum nominal diameter of the eccentric enlarged abrading head 28, and preferably at least about 40% larger than the maximum nominal diameter of the eccentric enlarged abrading head 28.

Preferably design parameters are selected so that the enlarged abrading head 28 is sufficiently eccentric that, when rotated over a stationary guide wire 15 at a speed between about 20,000 rpm and about 200,000 rpm, at least a portion of its tissue removing surface 37 rotates through a path (whether or not such path is perfectly regular or circular) with a maximum diameter that is substantially larger than the maximum nominal diameter of the eccentric enlarged abrading head 28. In various embodiments, the present invention is capable of defining a substantially orbital path with a maximum diameter that is incrementally between at least about 50% and about 400% larger than the maximum nominal diameter of the eccentric enlarged abrading head 28. Desirably such orbital path comprises a maximum diameter that is between at least about 200% and about 400% larger than the maximum nominal diameter of the eccentric enlarged abrading head 28.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A high-speed rotational atherectomy device for opening a stenosis in an artery having a given diameter, comprising:
 a guide wire having a maximum diameter less than the diameter of the artery;

a flexible elongated, rotatable drive shaft advanceable over the guide wire, the drive shaft having a rotational axis; and at least one eccentric abrading head fixedly attached to the drive shaft, the at least one eccentric abrading head having a non-flexible single piece unitary construction, the at least one eccentric abrading head comprising a center of mass having a positioning that is radially offset from the rotational axis of the drive shaft, the eccentric abrading head further comprising a proximal portion, an intermediate portion, and a distal portions, wherein the proximal portion comprises a proximal outer surface, the intermediate portion comprises an intermediate outer surface and the distal portion comprises a distal outer surface, the proximal outer surface having diameters that increase distally and a rounded proximal radiused edge, the rounded proximal radiused edge comprising a radius, the distal outer surface having diameters that decrease distally and a rounded distal radiused edge, the rounded distal radiused edge comprising a radius, wherein the radius of the rounded proximal radiused edge and the radius of the rounded distal radiused edge are substantially equivalent, and the intermediate outer surface being cylindrical, wherein at least the intermediate outer surface comprise tissue removal sections, wherein the proximal portion and the intermediate portion intersect and defining an edge at the intersection, and the intermediate portion and the distal portion intersect and defining an edge at the intersection wherein the at least one eccentric abrading head defines a drive shaft lumen therethrough and a hollow chamber, the hollow chamber having a size and shape, whereby the positioning of the center of mass of the at least one eccentric abrading head is at least partially determined, and wherein the drive shaft at least partially traverses the drive shaft lumen, wherein the at least one eccentric abrading head comprises a resting diameter and traverses an orbital pathway during high-speed rotation, wherein the orbital pathway traversed by the at least one eccentric abrading head is between about 200% to 400% larger than the resting diameter as a result of the eccentricity of the at least one eccentric abrading head.

2. The rotational atherectomy device of claim 1, wherein the portion of the drive shaft traversing the drive shaft lumen and attaching thereto comprises a single, unbroken drive shaft.

3. The rotational atherectomy device of claim 1, wherein the portion of the drive shaft traversing the drive shaft lumen and attaching thereto comprises at least two sections, each section attached to the drive shaft lumen with a gap between the at least two drive shaft sections.

4. The rotational atherectomy device of claim 1, wherein the proximal outer surface of the at least one eccentric abrading head is substantially defined by a lateral surface of a cone, the cone having an axis that intersects the rotational axis of the drive shaft.

5. The rotational atherectomy device of claim 4, wherein the distal outer surface of the at least one eccentric abrading head is substantially defined by a lateral surface of a cone, the cone having an axis that intersects the rotational axis of the drive shaft.

6. The rotational atherectomy device of claim 5 wherein the cone axis of the proximal outer surface and the cone axis of the distal outer surface intersect each other and are coplanar with the rotational axis of the drive shaft.

7. The rotational atherectomy device of claim 1, wherein the rounded proximal radiused edge comprises a tissue removal surface.

8. The rotational atherectomy device of claim 1, wherein the rounded distal radiused edge comprises a tissue removal surface.

9. The rotational atherectomy device of claim 1, wherein the proximal and distal outer surfaces comprise tissue removal sections.

10. The rotational atherectomy device of claim 1, wherein only the intermediate outer surface comprises a tissue removal section.

11. The rotational atherectomy device of claim 1 wherein the distal outer surface has diameters that increase distally at a generally constant rate, thereby forming generally the shape of a cone.

12. The rotational atherectomy device of claim 11 wherein the proximal outer surface has diameters that decrease distally at a generally constant rate, thereby forming generally the shape of a cone.

13. The rotational atherectomy device of claim 12 wherein opposing sides of each cone are at angle α of between about 10° and about 30° with respect to each other.

14. The rotational atherectomy device of claim 12 wherein opposing sides of each cone are at angle α of between about 20° and about 24° with respect to each other.

15. The rotational atherectomy device of claim 12 wherein each of the cones of the at least one eccentric abrading head has an axis that is not parallel to the rotational axis of the drive shaft.

16. The rotational atherectomy device of claim 12 wherein the axes of the cones of the at least one eccentric abrading head are coplanar and intersect the rotational axis of the drive shaft at an angle β of between about 2° and about 8°.

17. The rotational atherectomy device of claim 12 wherein the axes of the cones of the at least one eccentric abrading head are coplanar and intersect the rotational axis of the drive shaft at an angle β of between about 3° and about 6°.

18. The rotational atherectomy device of claim 1 wherein the proximal and distal outer surfaces of the at least one eccentric abrading head are substantially symmetrical to each other.

19. The rotational atherectomy device of claim 1 wherein the eccentric abrading head has a maximum diameter between about 1.0 mm and about 1.5 mm, and the center of mass is spaced away from the rotational axis of the drive shaft by a distance of at least about 0.013 mm.

20. The rotational atherectomy device of claim 1 wherein the eccentric abrading head has a maximum diameter between about 1.5 mm and about 1.75 mm, and the center of mass is spaced away from the rotational axis of the drive shaft by a distance of at least about 0.03 mm.

21. The rotational atherectomy device of claim 1 wherein the eccentric abrading head has a maximum diameter between about 1.75 mm and about 2.0 mm, and the center of mass is spaced away from the rotational axis of the drive shaft by a distance of at least about 0.06 mm.

22. The rotational atherectomy device of claim 1 wherein the eccentric abrading head has a maximum diameter of at least about 2.0 mm, and the center of mass is spaced away from the rotational axis of the drive shaft by a distance of at least about 0.1 mm.

23. The rotational atherectomy device of claim 1 wherein the eccentric abrading head has a maximum diameter between about 1.0 mm and about 1.5 mm, and the center of mass is spaced away from the rotational axis of the drive shaft by a distance of at least about 0.02 mm.

24. The rotational atherectomy device of claim 1 wherein the eccentric abrading head a maximum diameter between about 1.5 mm and about 1.75 mm, and the center of mass is spaced away from the rotational axis of the drive shaft by a distance of at least about 0.05 mm.

25. The rotational atherectomy device of claim 1 wherein the eccentric abrading head a maximum diameter between about 1.75 mm and about 2.0 mm, and the center of mass is spaced away from the rotational axis of the drive shaft by a distance of at least about 0.1 mm.

26. The rotational atherectomy device of claim 1 wherein the eccentric abrading head has a maximum diameter of at least about 2.0 mm, and the center of mass is spaced away from the rotational axis of the drive shaft by a distance of at least about 0.16 mm.

27. The rotational atherectomy device of claim 1 wherein a face of a transverse cross-section of the eccentric abrading head, taken at a position of maximum cross-sectional diameter of the eccentric abrading head has a geometric center spaced away from the rotational axis of the drive shaft.

28. The rotational atherectomy device of claim 27 wherein the eccentric abrading head has a maximum cross-sectional diameter between about 1.5 mm and about 1.75 mm, and the geometric center is spaced away from the rotational axis of the drive shaft by a distance of at least about 0.05 mm.

29. The rotational atherectomy device of claim 27 wherein the eccentric abrading head has a maximum cross-sectional diameter between about 1.75 mm and about 2.0 mm, and the geometric center is spaced away from the rotational axis of the drive shaft by a distance of at least about 0.1 mm.

30. The rotational atherectomy device of claim 27 wherein the eccentric abrading head has a maximum cross-sectional diameter of at least about 2.0 mm, and the geometric center is spaced away from the rotational axis of the drive shaft by a distance of at least about 0.15 mm.

31. The rotational atherectomy device of claim 27 wherein the eccentric abrading head has a maximum cross-sectional diameter between about 1.0 mm and about 1.5 mm, and the geometric center is spaced away from the rotational axis of the drive shaft by a distance of at least about 0.035 mm.

32. The rotational atherectomy device of claim 27 wherein the eccentric abrading head has a maximum cross-sectional diameter between about 1.5 mm and about 1.75 mm, and the geometric center is spaced away from the rotational axis of the drive shaft by a distance of at least about 0.07 mm.

33. The rotational atherectomy device of claim 27 wherein the eccentric abrading head has a maximum cross-sectional diameter between about 1.75 mm and about 2.0 mm, and the geometric center is spaced away from the rotational axis of the drive shaft by a distance of at least about 0.15 mm.

34. The rotational atherectomy device of claim 27 wherein the eccentric abrading head has a maximum cross-sectional diameter of at least about 2.0 mm, and the geometric center is spaced away from the rotational axis of the drive shaft by a distance of at least about 0.25 mm.

35. The rotational atherectomy device of claim 27 wherein the eccentric abrading head has a maximum cross-sectional diameter between about 1.5 mm and about 1.75 mm, and the geometric center is spaced away from the rotational axis of the drive shaft by a distance of at least about 0.09 mm.

36. The rotational atherectomy device of claim 27 wherein the eccentric abrading head has a maximum cross-sectional diameter between about 1.75 mm and about 2.0 mm, and the geometric center is spaced away from the rotational axis of the drive shaft by a distance of at least about 0.20 mm.

37. The rotational atherectomy device of claim 27 wherein the eccentric abrading head has a maximum cross-sectional diameter of at least about 2.0 mm, and the geometric center is spaced away from the rotational axis of the drive shaft by a distance of at least about 0.30 mm.

38. The rotational atherectomy device of claim 1 wherein the tissue removal surfaces are abrasive surfaces.

* * * * *